(12) United States Patent
Miller et al.

(10) Patent No.: US 11,027,089 B2
(45) Date of Patent: Jun. 8, 2021

(54) HEATING ARRANGEMENTS FOR HUMIDIFICATION SYSTEMS

(71) Applicant: Fisher & Paykel Healthcare Limited, Auckland (NZ)

(72) Inventors: Jeremy Livingston Miller, Auckland (NZ); Nordyn Alami, Auckland (NZ); Andrew John Partington, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 0 days.

(21) Appl. No.: 16/722,688

(22) Filed: Dec. 20, 2019

(65) Prior Publication Data

US 2020/0147335 A1    May 14, 2020

Related U.S. Application Data

(63) Continuation of application No. 15/999,210, filed on Aug. 17, 2018, now Pat. No. 10,537,699, which is a
(Continued)

(51) Int. Cl.
    *B01F 3/04*    (2006.01)
    *F24F 3/00*    (2006.01)
    (Continued)

(52) U.S. Cl.
    CPC .......... *A61M 16/109* (2014.02); *A61M 16/16* (2013.01); *B01F 3/04099* (2013.01);
    (Continued)

(58) Field of Classification Search
    CPC ................ A61M 16/16; A61M 16/109; A61M 16/1075; F24F 3/14; B01F 3/04099
    See application file for complete search history.

(56) References Cited

U.S. PATENT DOCUMENTS

| 3,757,082 A | 9/1973 | Goicoechea |
| 5,930,459 A | 7/1999 | Eckman et al. |

(Continued)

FOREIGN PATENT DOCUMENTS

| WO | WO 2008/148154 | 12/2008 |
| WO | WO 2012/171072 | 12/2012 |

OTHER PUBLICATIONS

International Search Report, PCT/IB2016/057905, dated Mar. 22, 2017, 4 pages.
(Continued)

*Primary Examiner* — Robert A Hopkins
(74) *Attorney, Agent, or Firm* — Knobbe, Martens, Olson & Bear, LLP

(57) ABSTRACT

An electrically conductive plastic (ECP) material can be used to heat water in a reservoir of a respiratory humidifier to encourage heating and/or humidification of gases passing through the respiratory humidifier. The electrically conductive plastic material can at least in part overmould the base and/or walls of the chamber and/or the reservoir of the respiratory humidifier. The reservoir can also partially or fully be formed from the electrically conductive plastic
(Continued)

material. Furthermore, the humidification system can be configured to create substantially equal or differential heating of water in the reservoir.

20 Claims, 17 Drawing Sheets

Related U.S. Application Data continuation of application No. 14/660,122, filed on Mar. 17, 2015, now Pat. No. 10,052,449.

(60) Provisional application No. 61/968,500, filed on Mar. 21, 2014.

(51) Int. Cl.
*A61M 16/10* (2006.01)
*A61M 16/16* (2006.01)
*F24F 3/14* (2006.01)
*A61M 16/00* (2006.01)
*A61M 16/06* (2006.01)

(52) U.S. Cl.
CPC ........... *F24F 3/14* (2013.01); *A61M 16/0066* (2013.01); *A61M 16/06* (2013.01); *A61M 16/1095* (2014.02); *A61M 2205/0283* (2013.01); *A61M 2205/3368* (2013.01); *A61M 2205/3673* (2013.01); *A61M 2206/14* (2013.01); *A61M 2207/00* (2013.01)

(56) References Cited

U.S. PATENT DOCUMENTS

| 8,550,072 | B2 | 10/2013 | Thudor et al. |
| 8,833,364 | B2 | 9/2014 | Buchberger |
| 8,873,941 | B2 * | 10/2014 | Row .................. A61M 16/109 |
| | | | 392/386 |
| 10,052,449 | B2 | 8/2018 | Miller et al. |
| 10,537,699 | B2 | 1/2020 | Miller et al. |
| 2002/0086194 | A1 | 7/2002 | Blaszczyk et al. |
| 2004/0102731 | A1 | 5/2004 | Blackhurst et al. |
| 2004/0118401 | A1 | 6/2004 | Smith et al. |
| 2010/0147299 | A1 | 6/2010 | Row et al. |
| 2010/0234794 | A1 | 9/2010 | Weadock et al. |
| 2013/0081618 | A1 | 4/2013 | Korneff et al. |
| 2013/0272338 | A1 | 10/2013 | Lieberman |
| 2014/0131904 | A1 | 5/2014 | Tang et al. |
| 2014/0251338 | A1 | 9/2014 | Asvadi et al. |
| 2014/0352694 | A1 | 12/2014 | Row et al. |
| 2015/0030317 | A1 | 1/2015 | Bayer et al. |
| 2015/0233588 | A1 | 8/2015 | Betts et al. |
| 2015/0265796 | A1 | 9/2015 | Miller et al. |
| 2018/0361104 | A1 | 12/2018 | Boyes et al. |

OTHER PUBLICATIONS

European Extended Search report for EP Application No. 16877882.7 dated Jul. 31, 2019 in 9 pages.

* cited by examiner

HEATING ARRANGEMENTS FOR HUMIDIFICATION SYSTEMS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention generally relates to humidification devices. More particularly, the present invention relates to heating arrangements for use with respiratory devices.

Description of the Related Art

Respiratory disorders deal with the inability of a sufferer to effect a sufficient exchange of gases with the environment, leading to an imbalance of gases in the sufferer. These disorders can arise as a pathological consequence of an obstruction of the airway, insufficiency of the lungs in generating negative pressure, an irregularity in the nervous function of the brain stem, or some other physiological complication. Treatment of such disorders is diverse and depends on the particular respiratory disorder being targeted. In the first instance, a constriction of the airway, otherwise known as an obstructive apnea or a hypopnea (collectively referred to as obstructive sleep apnea or OSA), can occur when the muscles that normally keep the airway open in a patient relax during slumber to the extent that the airway is constrained or completely closed off, a phenomenon often manifesting itself in the form of snoring. When this occurs for a significant period of time, the patient's brain typically recognizes the threat of hypoxia and partially wakes the patient in order to open the airway so that normal breathing may resume. The patient may be unaware of these occurrences, which may occur as many as several hundred times per session of sleep. This partial awakening may significantly reduce the quality of the patient's sleep, over time potentially leading to a variety of symptoms, including chronic fatigue, elevated heart rate, elevated blood pressure, weight gain, headaches, irritability, depression and anxiety.

Obstructive sleep apnea is commonly treated with the application of positive airway pressure (PAP) therapy. PAP therapy involves delivering a flow of gas to a patient at a therapeutic pressure above atmospheric pressure that will reduce the frequency and/or duration of apneas, hypopneas, and/or flow limitations. This therapy is often delivered by using a positive airway pressure device (PAP device) to propel a pressurized stream of air through a conduit to a patient through an interface or mask located on the face of the patient. The stream of air may be heated to near body temperature. The stream of air may be humidified. The humidification may be performed by forcing the stream of air to travel through a respiratory humidifier containing water and a heater for heating the water. In such a system, the heater encourages the evaporation of the water, which in turn imbues the stream of air with moisture and/or heat. This moisture and/or heat may help to ameliorate discomfort that may arise from the use of unhumidified PAP therapy. Respiratory humidifiers may also be used with other gas-based therapies, such as high flow therapy, and may have similar therapeutic benefits when used with other gas-based therapies.

SUMMARY OF THE INVENTION

In some cases, when utilizing a respiratory therapy system involving the administration of gases, it is desired to use a respiratory humidifier to heat and/or humidify the gases being delivered to a patient. The respiratory humidifier may comprise a humidification chamber comprising a resistive metallic heating plate and a reservoir that may interface with the resistive metallic heating plate. The gas may pass through the reservoir and/or humidification chamber. The resistive metallic heating plate may be used to heat liquid contained in the reservoir to encourage liquid entrainment in the gas flow. However, there may be difficulty in the industrial use of some such resistive metallic heating plates. Many metals may be difficult and/or expensive to mold into desired shapes. The price of the raw material used to craft a resistive metallic heating plate may be high. The electrical and/or thermal conductivity of the resistive metallic heating plate may not be ideal. A resistive metallic heating plate, if used in a humidification chamber, may not blend seamlessly with the rest of the humidification chamber, and may not be aesthetically pleasing to a consumer. Accordingly, it is an object of the disclosure to provide an improved heating system that might solve one or more of the above problems, or at least provide the public with a useful choice.

Thus, in accordance with at least one of the embodiments disclosed herein, a humidifier is disclosed. The humidifier may be a respiratory humidifier. The humidifier may comprise a reservoir. The humidifier may comprise a base. The base may define a region configured to accommodate the reservoir. The humidifier may comprise a chamber for receiving the reservoir. The heater may be located in or may form part of the base and/or reservoir and/or chamber. The heater may at least in part be constructed from an electrically conductive plastic material. The base may be part of a chamber. The heater may be configured to promote differential heating of liquid in the reservoir. The heater may have a variable thickness along its length and/or width.

In some configurations, the heater may be directly or indirectly connected to a source of power. In some configurations, the heater may be connected to the source of power by an electrical conductor. In some configurations, the heater may be wirelessly connected to the source of power.

In some configurations, the base may be at least partially overmoulded with the heater. In some configurations, the base is at least in part discontinuously overmoulded with the heater. In some configurations, the base is fully or completely overmoulded with the heater.

In some configurations, the reservoir has at least partially been formed from the heater. In some configurations, the reservoir has discontinuous portions at least partially formed from the heater. In some configurations, the reservoir has been wholly formed from the heater.

In some configurations, the reservoir comprises a bottom section. The heater may at least partially overmould the bottom section. In some configurations, the heater may fully overmould the bottom section. In some configurations, the reservoir comprises a side wall. The heater may at least partially overmould the side wall. In some configurations, the heater may fully overmould the side wall. In some configurations, the heater may have an irregular thickness. The irregular thickness may be along the width and/or length of the heater. In some configurations, the electrically conductive plastic material comprises polyphenylene sulfide.

In accordance with another embodiment disclosed herein, a humidifier is disclosed. The humidifier may comprise a chamber for receiving a reservoir. The humidifier may comprise a heater for heating liquid in the reservoir. The heater may be located in or form part of the chamber. The humidifier may comprise a reservoir and the heater may be located in or form part of the reservoir. The heater may be configured to promote differential heating of liquid in the reservoir. The heater may comprise a variable thickness along its length and/or width.

In accordance with another embodiment disclosed herein, a humidification system is disclosed. The humidification system may comprise a heater having a variable thickness along its length and/or width. The heater may comprise a contoured first surface that comprises two crests separated by a trough. The trough may be positioned along the heater at an off centre location. The humidification system may comprise electrical connectors at opposing ends of the trough. The humidification system may comprise a reservoir. The heater may be present in the reservoir. The humidification system may comprise a chamber. The heater may be present in the chamber.

BRIEF DESCRIPTION OF THE DRAWINGS

Certain features, aspects and advantages of specific embodiments and modifications of the present invention will become apparent to those skilled in the art from the detailed description herein having reference to the figures that follow, of which.

DETAILED DESCRIPTION OF SPECIFIC EMBODIMENTS

Certain features, aspects and advantages of at least one of the configurations disclosed herein include the realization that an electrically conductive plastic (ECP) material may be used as a heater for assisting in the heating and/or humidification of gases delivered by a respiratory therapy system. The ECP material may, for example, be used in a respiratory humidifier to heat water contained in a reservoir such that water vapour may be generated. The water vapour may join gases passing through the respiratory humidifier and/or reservoir to provide humidified gases to a patient.

Figure 1:
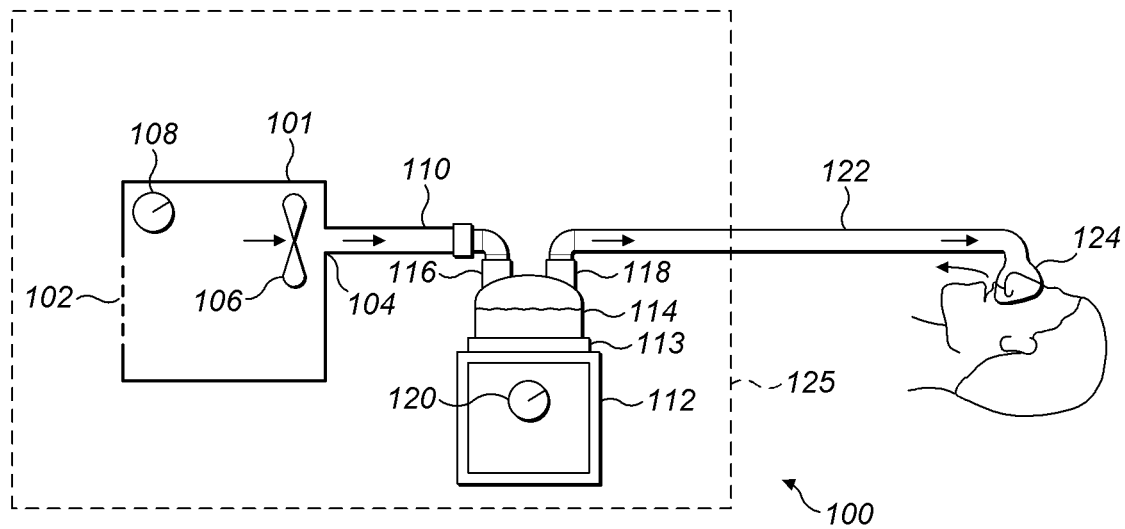
FIG. 1 shows a schematic diagram of a respiratory therapy system.

With reference to FIG. 1, a configuration for a respiratory therapy system 100 is shown. In the illustrated configuration, the respiratory therapy system 100 may comprise a flow generator 101. The flow generator 101 may comprise a gas inlet 102 and a gas outlet 104. The flow generator may comprise a blower 106. The blower 106 may comprise a motor. The motor may comprise a stator and a rotor. The rotor may comprise a shaft. An impeller may be linked to the shaft. In use, the impeller may rotate concurrently with the shaft to draw in gas from the gas inlet 102. The flow generator 101 may comprise a user interface 108 which may comprise one or more buttons, knobs, dials, switches, levers, touch screens, and/or displays so that a user might view data related to the operation of the flow generator 101 or to other components of the respiratory therapy system 100 or input operation parameters into the flow generator 101 to control its operation or the operation of other components of the respiratory therapy system 100. The flow generator 101 may pass gas through the gas outlet 104 to a first conduit 110. The first conduit 110 may pass the gas to a humidifier 112 that may entrain moisture in the gas to provide a humidified gas stream. The humidifier 112 may comprise a humidifier inlet 116 and a humidifier outlet 118. The humidifier 112 may comprise a reservoir 114 that may be filled with water or some other humidifying agent (hereinafter referred to as water). The humidifier 112 may comprise a chamber (not shown). The chamber may serve as a housing or support for the reservoir 114. The humidifier 112 may comprise a heater 113 that may be used to heat the water in the reservoir 114 to encourage water vaporization and/or entrainment in the gas flow and/or increase the temperature of gases passing through the humidifier 112. The humidifier 112 may have a user interface 120 which may comprise one or more buttons, knobs, dials, switches, levers, touch screens, and/or displays so that a user might input operation parameters into the humidifier 112 to view data related to the operation of the humidifier 112 or to other components of the respiratory therapy system 100 or control the operation of the heater 113 and/or operation of other aspects of the humidifier 112 or respiratory therapy system 100. Gas may then pass from the humidifier outlet 118 to a second conduit 122. The second conduit 122 may comprise a conduit heater (not shown) that may be used to add heat to gases passing through the second conduit 122. The heat may help to prevent the condensation of moisture entrained in the gas stream along the walls of the second conduit 122. The conduit heater may comprise one or more resistive wires located in, on, or around a wall of the second conduit 122. Gas passing through the second conduit 122 may then enter a patient interface 124 that may pneumatically link the respiratory therapy system 100 to the patient's airway. The patient interface 124 may comprise a nasal mask, an oral mask, an oro-nasal mask, a full face mask, a nasal pillows mask, a nasal cannula, an endotracheal tube, a combination of the above or some other gas conveying system.

In the illustrated configuration, and as implied above, the respiratory therapy system 100 may operate as follows. Gas may be drawn into the flow generator 101 through the gas inlet 102 due to the rotation of an impeller of the motor of the blower 106. Gas may then be propelled out of the gas outlet 104 and along the first conduit 110. The gas flow may enter the humidifier 112 through the humidifier inlet 116. Once in the humidifier 112, the gas may pick up moisture while passing over the water in the reservoir 114. The reservoir 114 may be heated by the heater 113, which may aid in the humidification and/or heating of the gas passing through the respiratory humidifier 112. The gas may leave the humidifier 112 through a humidifier outlet 118 and enter a second conduit 122. Gas may be passed from the second conduit 122 to the patient interface 124, where the gas may be taken into the patient's airways to aid in the treatment of respiratory disorders.

The illustrated configuration should not be taken to be limiting; many other configurations for the respiratory therapy system 100 are possible. In some configurations, the flow generator 101 may, for example, comprise a source or container of compressed gas (e.g. air). The container may comprise a valve that may be adjusted to control the flow of gas leaving the container. In some configurations, the flow generator 101 may use such a source of compressed gas and/or another gas source in lieu of a blower 106. In some configurations, the blower 106 may be used in conjunction with another gas source. In some configurations, the flow generator 101 may draw in atmospheric gases through the gas inlet 102. In some configurations, the flow generator 101 may be adapted to both draw in atmospheric gases through the gas inlet 102 and accept other gases (e.g. oxygen, nitric oxide, carbon dioxide, etc) through the same gas inlet 102 or a different inlet. In some configurations, the humidifier 112 can be integrated with the flow generator 101. In some configurations, the humidifier 112 and the flow generator 101 may share a housing 125. In some such configurations, only a single conduit extending between the flow generator 101 and the patient interface 124 need be used to convey gases to a patient. In some configurations, the flow generator 101 and the humidifier 112 may have a single user interface located on either the flow generator 101 or the humidifier 112. In some configurations, the operation of the flow generator 101, of the humidifier 112, or of other aspects of the respiratory therapy system 100 may be controlled by a controller. The controller may comprise a microprocessor. The controller may be located in or on the flow generator 101, the humidifier 112, or other parts of the respiratory therapy system 100. In some configurations, multiple controllers may be used. In some configurations, the operation of the flow generator 101, of the humidifier 112, or of other aspects of the respiratory therapy system 100 may be controlled wirelessly using a user interface located on a remote computing device. In some configurations, the respiratory therapy system 100 may comprise one or more sensors for detecting various characteristics of the gas, including pressure, flow rate, temperature, absolute humidity, relative humidity, enthalpy, oxygen concentration, and/or carbon dioxide concentration. Measurements obtained using the one or more sensors may be utilized by the controller to facilitate open or closed loop control of one or more components of the respiratory therapy system 100, including but not limited to the flow generator 101, the humidifier 112, the heater 113 and/or the conduit heater of the second conduit 122. In some configurations, there may be no user interface or a minimal user interface for the flow generator 101, humidifier 112, or other aspects of the respiratory therapy system 100. In some such configurations, the respiratory therapy system 100 may utilize a sensor to determine if the patient is attempting to use the respiratory therapy system 100. In such configurations, the respiratory therapy system may automatically operate (e.g., the flow generator 101 may propel gases, the humidifier 112 may humidify gases, etc.) according to one or more predetermined parameters if the sensor indicates that the patient is attempting to use the respiratory therapy system 100.

Attention is now given to the discussion of ECP materials. An ECP material may comprise a synthetic or natural resin, a plastic, a polymer, a composition of a resin, plastic, or polymer, or another material that is electrically conductive and has plastic qualities or characteristics. In some configurations, the ECP material may comprise a thermoplastic material, e.g., a material that becomes moldable or pliable if the temperature of the material is raised to a particular temperature and that returns to a solid, relatively firm state upon cooling. In some configurations, the ECP material may, for example, comprise plastics or polymers that are intrinsically electrically conductive, such as polyphenylene sulfides, polyacetylenes, polyanilines, polypyrroles, polythiophenes, polyphenylenes, polyphenylene vinylenes (such as poly(p-phenylene vinylene)), polyalkylthiophenes, polypyrenes, polyazulenes, polynaphthalenes, polycarbazoles, polyindoles, polyazepines, polyethylenedioxythiophenes (such as poly(3,4-ethylenedioxythiophene)), polymers comprising metal atoms, and polymer-metal complexes. In some configurations, the ECP material may comprise an electrically conductive additive or doping agent, such as carbon black, carbon fibers, carbon nanotubes, graphite, graphene, stainless steel fibers, metal flakes or powders (e.g. gold, silver, copper, etc), metal composites, organometallic complexes, phthalocyanine salts, and polycyclic aromatic hydrocarbons. In some such configurations, plastics or polymers that are not intrinsically electrically conductive may be used. Preferably, the ECP material may be suitable for use as a resistive heater.

Figure 4A:
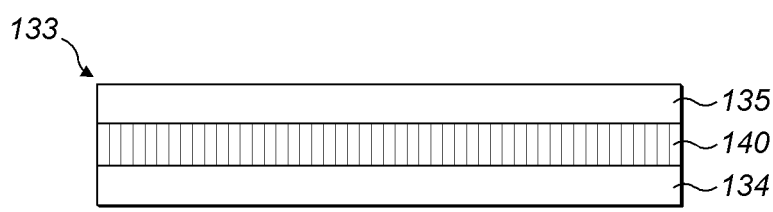
FIG. 4A illustrates a configuration for an electrically conductive plastic material.
Figure 4B:
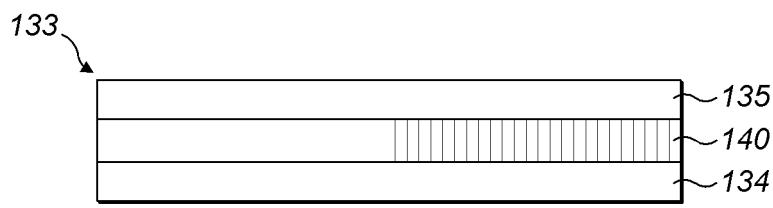
FIG. 4B illustrates a configuration for an electrically conductive plastic material.
Figure 4C:
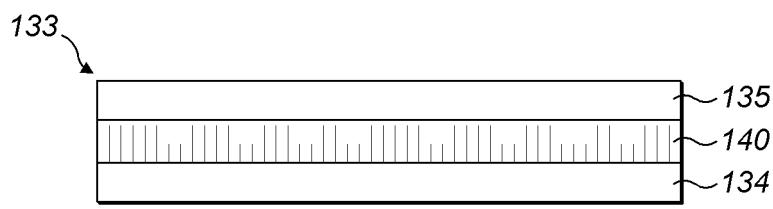
FIG. 4C illustrates a configuration for an electrically conductive plastic material.
Figure 4D:
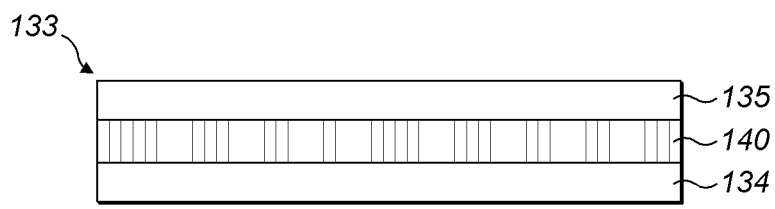
FIG. 4D illustrates a configuration for an electrically conductive plastic material.
Figure 4E:
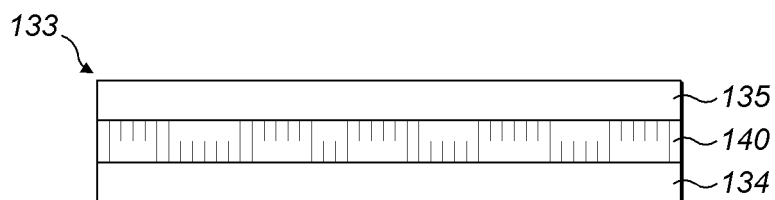
FIG. 4E illustrates a configuration for an electrically conductive plastic material.
Figure 4F:
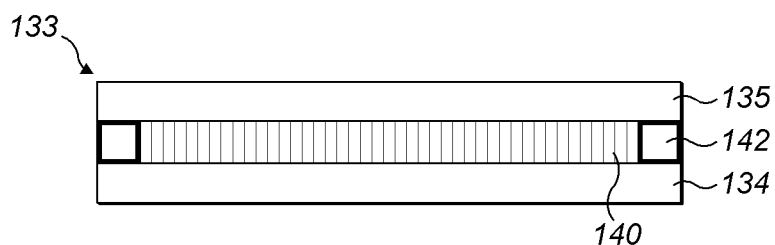
FIG. 4F illustrates a configuration for an electrically conductive plastic material.

With reference to FIGS. 4A-4F, an ECP structure 133 is shown. The ECP structure 133 may comprise an ECP material layer 140. In the illustrated configuration, the ECP material layer 140 is the form of a film. However, the ECP material layer 140 may comprise other geometries, such as strands or blocks. In some configurations, the ECP structure 133 may comprise a first supporting layer 134 and/or a second supporting layer 135. The layer of ECP material 140 may be in physical communication with the first or second supporting layers 134, 135. Alternatively, the layer of ECP material 140 may be in physical communication with both the first and second supporting layers 134, 135 so that the ECP layer 140 is substantially sandwiched between the first and second supporting layers 134, 135. The first supporting layer 134 and/or second supporting layer 135 may likewise be in the form of films, or the first and/or second supporting layers 134, 135 may comprise other geometries. The first and/or second supporting layers 134, 135 may comprise thermally conductive and/or electrically insulative materials. The layer of ECP material 140, first supporting layer 134, and/or second supporting layer 135 may be bound together. The binding may be realized through the use of a mechanical fastener, an adhesive, lamination, ultrasonic welding, or through the use of some other binding process or device. In some configurations, the layer of ECP material 140, the first supporting layer 134, and/or the second supporting layers 135 may be a part of an apparatus, for example, a wall or base of a humidification chamber, a wall or base of a reservoir, of another component of a humidifier, a patient interface (for example, in or on an internal surface of a patient interface, the internal surface being a surface upon which condensed water may be deposited in use), a conduit (for example, as a conduit heater) or of some other respiratory apparatus. As demonstrated in FIG. 4A, the ECP material layer 140 may be entirely constructed from an ECP material. However, in some configurations, the ECP material layer 140 may at least in part be constructed from another material. As shown in FIG. 4B, the ECP material layer 140 may be constructed from a section of an ECP material and a section of another material. As shown in FIG. 4C, the ECP material layer 140 may be constructed from a first section of ECP material and a second section opposing the first section of another material, where the first section of ECP material has an irregular thickness along the width and/or length of the ECP material layer 140. As shown in FIG. 4D, the ECP material layer 140 may be constructed from alternating sections of an ECP material and one or more other materials. As shown in FIG. 4E, the ECP material layer 140 may comprise a serpentine track of ECP material in or on another material. Many other configurations may be imagined. The configurations shown in FIGS. 4B-4E may be useful for creating differential heating in a body of water heated by the ECP structure 133, which may encourage the formation of convection currents, eddies, and/or other turbulence-inducing phenomena in the body of water such that efficient mixing and/or heating of the water may be realized. Additionally, in some configurations, and as shown in FIG. 4F, the ECP material layer 140 and/or other parts of the ECP structure 133 may interface with an electrical structure 142 that may convey electrical and/or thermal energy to the ECP structure 133 and/or ECP material layer 140. The electrical structure 142 may comprise metals (e.g. aluminum bars or other masses) or other electrically conductive materials. The electrical structure 142 may in turn receive electrical energy wirelessly or through a wired connection or electrical lead. The electrical lead may come from a component of a respiratory therapy system, such as, for example, a flow generator or a heated conduit of a respiratory therapy system.

Figure 2:
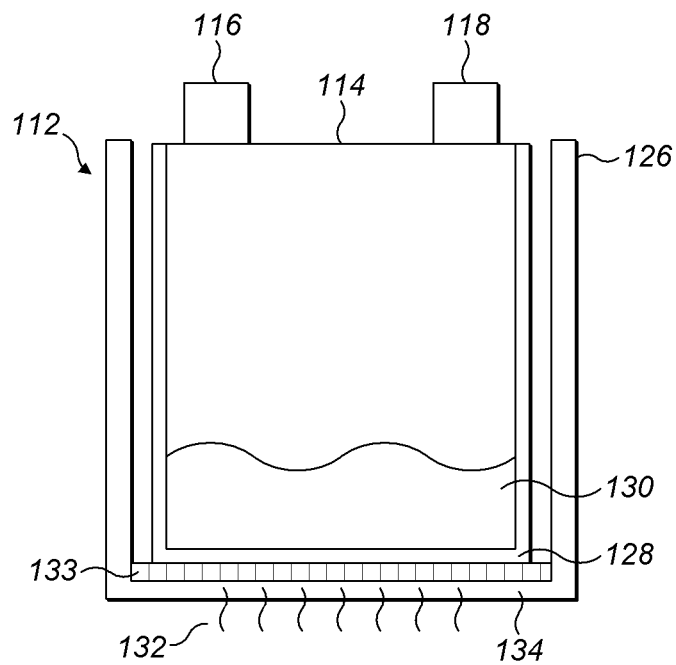
FIG. 2 illustrates a humidifier configuration in which a base of a chamber of the humidifier has been overmoulded with an electrically conductive plastic material.
Figure 3:
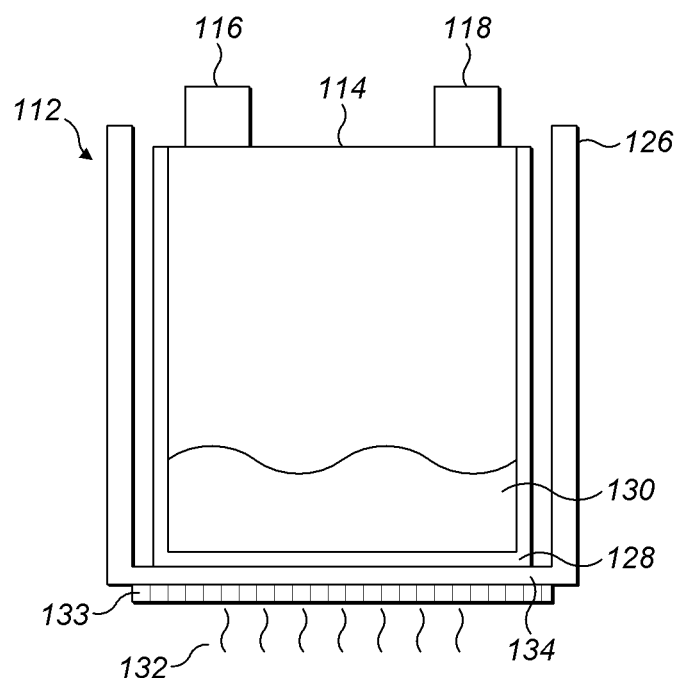
FIG. 3 illustrates a humidifier configuration in which a base of a chamber of the humidifier has overmoulded an electrically conductive plastic material.

With reference to FIG. 2, a humidifier 112 is shown. The humidifier 112 may comprise a reservoir 114 that may in use hold water 130 or another humidification agent (hereinafter referred to as water 130). The reservoir 114 may comprise a gas inlet 116 and a gas outlet 118. The humidifier 112 may comprise a humidification chamber 126 that may in use accommodate or otherwise define a space for the placement of the reservoir 114. In some configurations, the humidification chamber 126 may comprise a gas inlet. The gas inlet of the humidification chamber 126 may pneumatically interface with the gas inlet 116 of the reservoir 114. In some configurations, the humidification chamber 126 may comprise a gas outlet. The gas outlet of the humidification chamber 126 may pneumatically interface with the gas outlet 118 of the reservoir 114. Many different configurations of inlets and outlets for the humidifier 112 may be possible. For example, in some configurations, the humidification chamber 126 and the reservoir 114 may share a single conjoined gas inlet that extends from an outer wall of the humidification chamber 126 to an inner wall of the reservoir 114. In some configurations, the humidification chamber 126 and the reservoir 114 may share a single conjoined gas outlet that extends from an inner wall of the reservoir 114 to an outer wall of the humidification chamber 126. In the illustrated configuration of FIG. 2, the humidification chamber 126 comprises a base 134. The base 134 may be overmoulded with an ECP structure 133. In some configurations, and as demonstrated in FIG. 3, the base may overmould the ECP structure 133. In other configurations, the ECP structure 133 may be secured to the base 134 through the use of other methods, including but not limited to welding (for example, ultrasonic or high frequency welding), the use of adhesives, or the use of mechanical fastening arrangements (for example, hook-and-loop fasteners, screw threading arrangements, bolts, etc). The ECP structure 133 may directly or indirectly interface with an electrical connection 132. The electrical connection 132 may include, for example, a wire or conductor that may be electrically linked to a battery, a fuel cell, an AC power source or a DC power source. The electrical connection 132 may interface with the ECP layer 133 in a variety of ways. In some configurations, the electrical connection 132 may include a wire that may protrude through the base 134 of the humidification chamber 126 or some other wall of the humidification chamber 126 or opening in the humidification chamber 126 (for example, a gas inlet or gas outlet of the humidification chamber 126) to interface with the ECP structure 133. In some configurations, no direct electrical connection 132 is necessary to supply the ECP structure 133 with electrical energy. For example, the ECP structure 133 may receive electrical energy wirelessly by inductive charging or resonant inductive coupling. The ECP structure 133 may be energized using inductive electrical power transfer technology. In some configurations, the technology may be similar to technologies used for the Qi interface standard for charging mobile devices. In use, the ECP structure 133 may receive electrical current from the electrical connection 132 or some other source of electricity. The ECP structure 133 converts the electrical energy into thermal energy. The thermal energy is passed to the reservoir 114 containing water 130. In some configurations, the thermal energy generated may be passed to the reservoir 114 through a thermally conductive element. The thermally conductive element may be part of a base 128 or wall of the reservoir 114, may be part of the humidification chamber 126, or may be part of both the reservoir 114 and the humidification chamber 126. Thermal energy may pass from the reservoir 114 to the water 130 in the reservoir 114 to heat the water. Water vapor may be generated from the water 130 which then may join the flow of gases passing from the gas inlet 116 to the gas outlet 118. In some configurations, the thermally conductive element may not be present. In some configurations, the reservoir 114 may be wholly constructed from a thermally conductive material. Advantageously, the ECP structure 133 may be used to quickly heat the water 130 while being easy to form into desired shapes using conventional molding techniques. Additionally, the cost of the raw materials used to form the ECP structure 133 may be less than the cost for other more conventional materials usable for heating water 130 in respiratory humidification systems. The ECP structure 133 and/or other components of the humidifier 122 may comprise or interface with one or more thermistors, thermocouples, or other sensors or sensing modules that may be used to help control operation of the humidifier 112 or other parts of a respiratory therapy system 100.

Figure 5A:
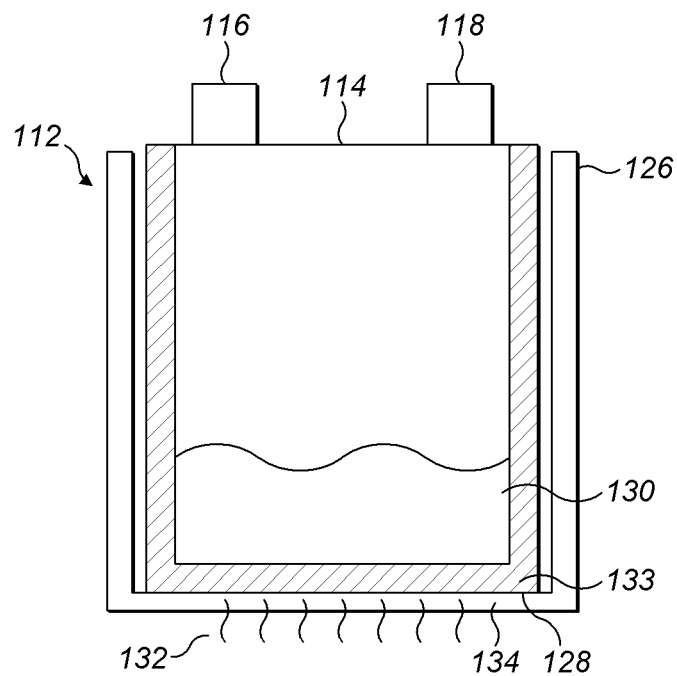
FIG. 5A illustrates a humidifier configuration wherein the entire reservoir has been constructed from an electrically conductive plastic material.
Figure 5B:
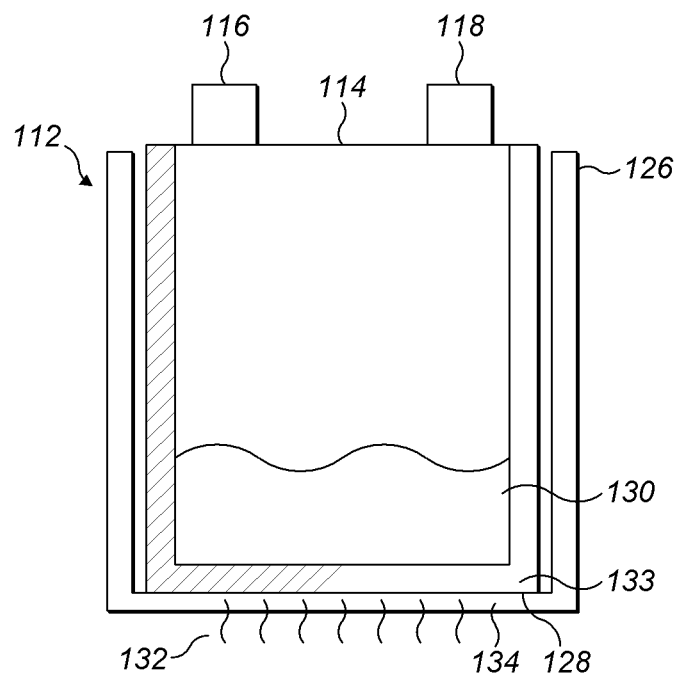
FIG. 5B illustrates a humidifier configuration wherein a part of the reservoir has been constructed from an electrically conductive plastic material.
Figure 5C:
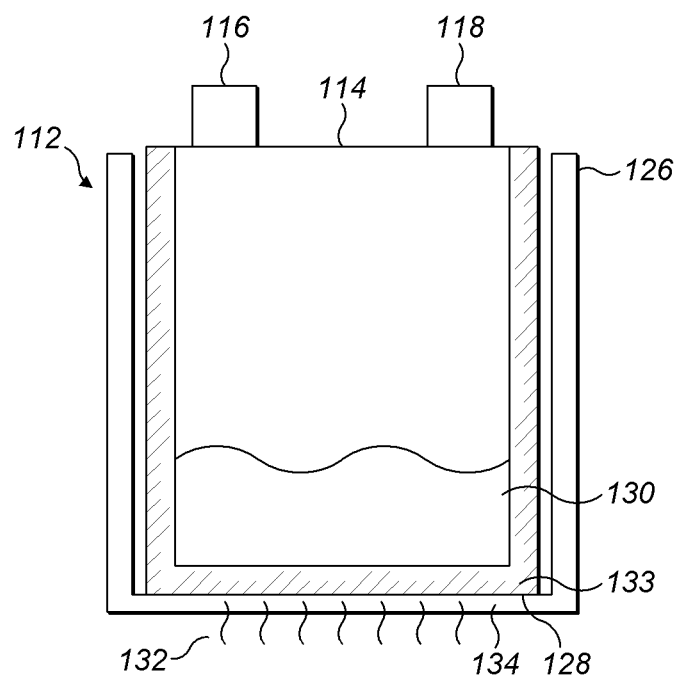
FIG. 5C illustrates a humidifier configuration wherein a part of the reservoir has been constructed from an electrically conductive plastic material.
Figure 5D:
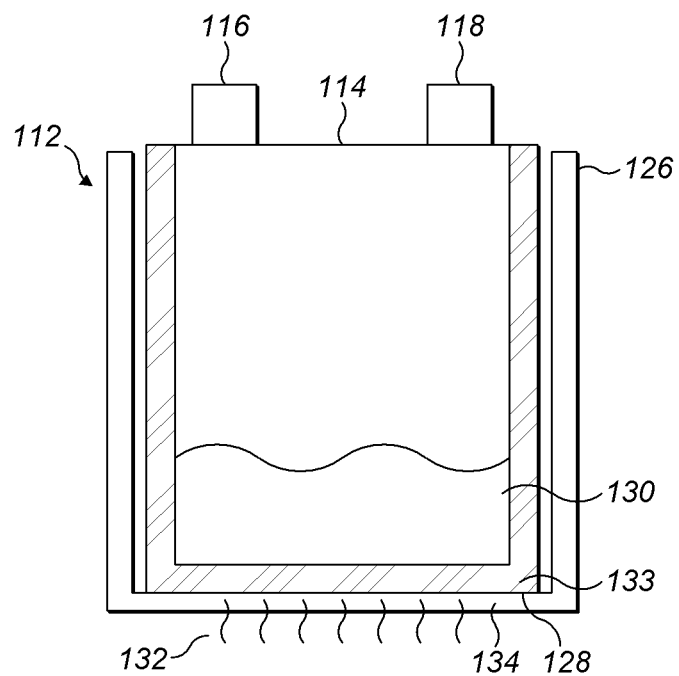
FIG. 5D illustrates a humidifier configuration wherein a part of the reservoir has been constructed from an electrically conductive plastic material.
Figure 5E:
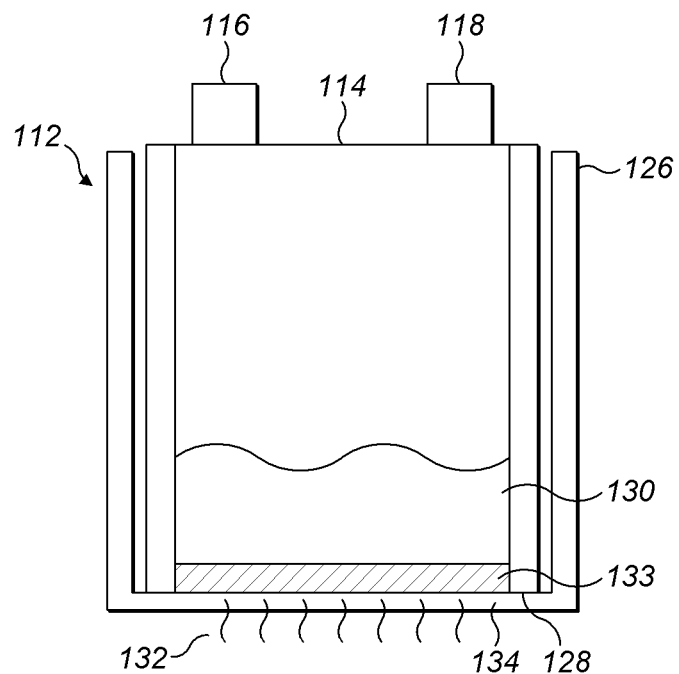
FIG. 5E illustrates a humidifier configuration wherein a part of the reservoir has been constructed from an electrically conductive plastic material.
Figure 5F:
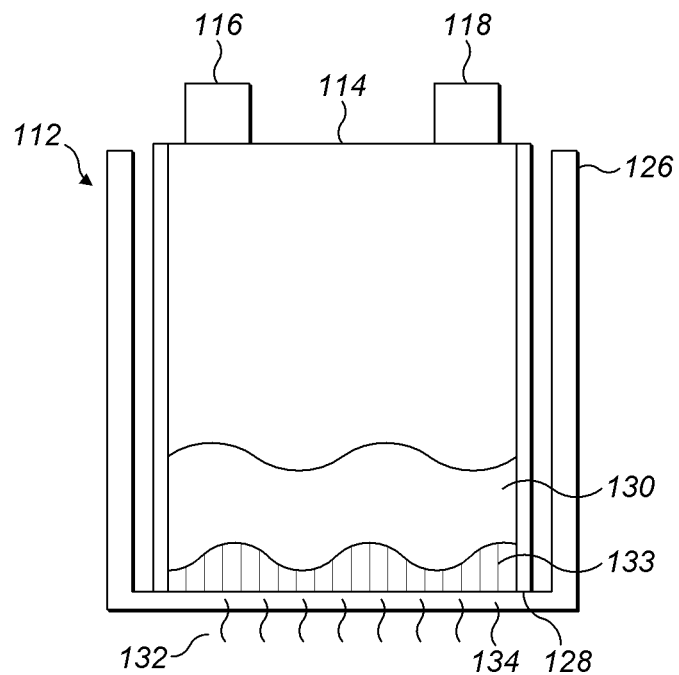
FIG. 5F illustrates a humidifier configuration wherein a part of the reservoir has been constructed from an electrically conductive plastic material.
Figure 5G:
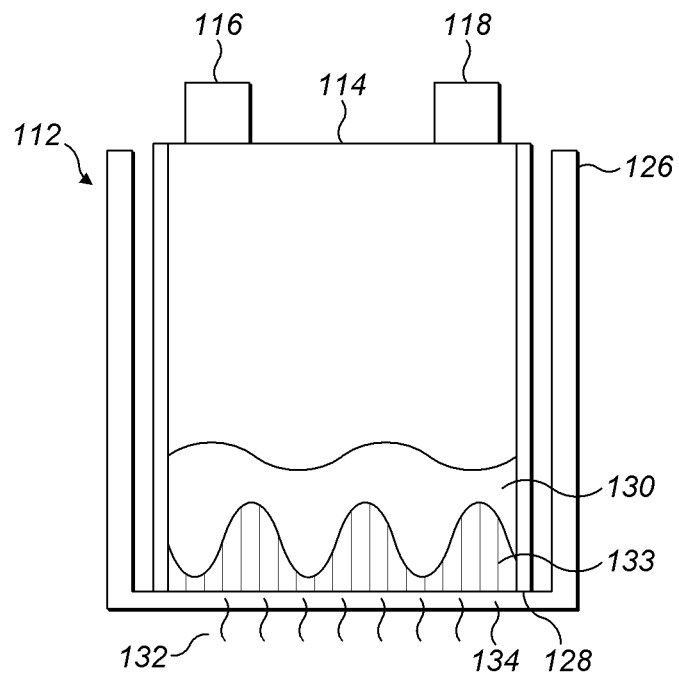
FIG. 5G illustrates a humidifier configuration wherein a part of the reservoir has been constructed from an electrically conductive plastic material.

In some configurations, and as demonstrated in FIGS. 5A-5G, the reservoir 114 may be constructed at least in part from an ECP structure 133. In some such configurations, the humidification chamber 126 need not comprise a heating material or separate ECP structure along the base 134 or walls of the humidification chamber 126. The electrical connection 132 may interface directly with one or more sections of the reservoir 114. In other configurations, electrical energy may be delivered to the reservoir 114 wirelessly as similarly described elsewhere in this disclosure with reference to FIGS. 2 and 3. In some configurations, and as illustrated in FIG. 5A, the entire reservoir 114 may be constructed from an ECP structure 133. However, in some configurations, only a part of the reservoir 114 may be constructed from an ECP structure 133. As shown in FIG. 5B, the reservoir 114 may be constructed from a section of an ECP structure 133 and a section of another material, such as a non-thermally conductive and/or non-electrically conductive material. The sections may be on opposite sides of the reservoir 114. As shown in FIG. 5C, the reservoir 114 may be constructed from a first section of an ECP structure 133 and a second section opposing the first section of another material, where the first section has an irregular thickness along the width and/or length of the first section. As shown in FIG. 5D, the reservoir 114 may be constructed from alternating sections of an ECP structure 133 and one or more other materials. As shown in FIG. 5E, the base 128 of the reservoir 114 may be constructed from an ECP structure 133. As shown in FIGS. 5F and 5G, the base 128 of the reservoir 114 constructed from the ECP structure 133 may have an irregular thickness along the width and/or length of the base 128. In some configurations, and particularly in the configurations illustrated in FIGS. 5B, 5C, 5D, 5F, and 5G, differential heating of the water 130 in the reservoir 114 may occur. The differential heating may encourage the formation of convection currents, eddies, and/or other turbulence-inducing phenomena in the body of water such that efficient mixing and/or heating of the water 130 may be realized. The differential heating effect may be improved as the contact area of the ECP structure 133 with the water 130 increases. For example, in some configurations, the humidifier configuration demonstrated in FIG. 5G may be more preferable than the humidifier configuration demonstrated in FIG. 5F. In some configurations, part or all of the ECP structure 133 may be constructed from porous materials and/or may comprise microstructures or features, such as ridges, ribs, depressions, and/or fenestrations, for example but without limitation. The porous materials and/or microstructures or features may improve the contact area between the ECP structure 133 and the water 130. Electrical current from an electrical connection 132 or some other source of electricity may be fed into the reservoir 114 at one or more points along, in, or on the reservoir comprising the ECP structure 133. In some configurations, different levels of electrical energy may be applied to different sections or portions of the ECP structure 133. In use, the humidification chamber 126 may serve to electrically and/or thermally isolate the reservoir 114. In some configurations, the humidification chamber 126 need not be present. In some such configurations, the reservoir 114 (and electrical connection 132, if present) may comprise the entirety of the respiratory humidifier 112 (e.g. the chamber 126 may not be present).

Figure 6:
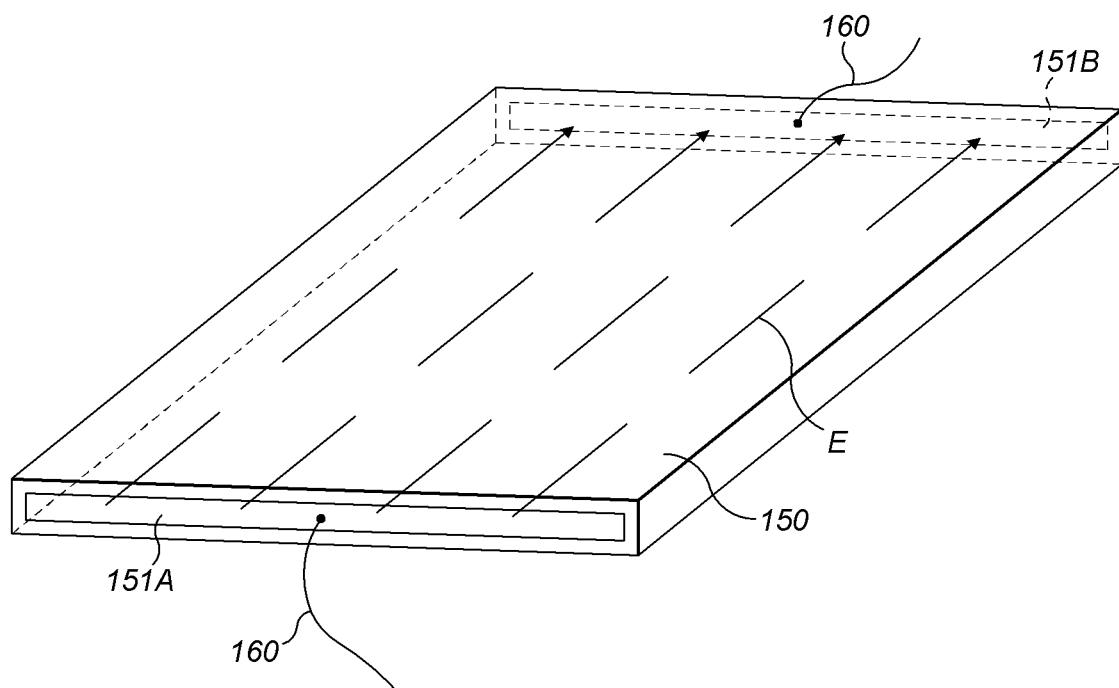
FIG. 6 shows a schematic diagram of current pathways across a configuration for a humidifier heater.
Figure 7:
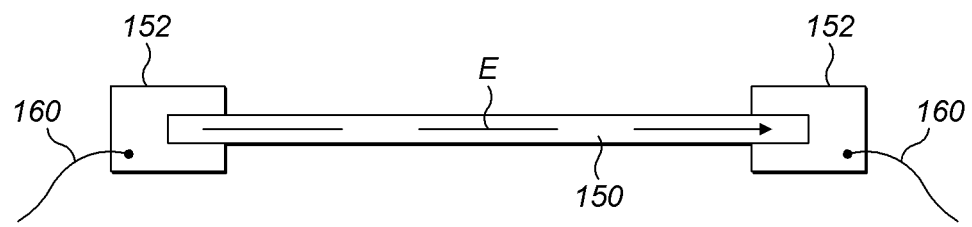
FIG. 7 shows another schematic diagram of current pathways across a configuration for a humidifier heater.

In some configurations, if an electrical current is passed from point to point across a heater comprising electrically conductive material and having a substantially uniform shape and configuration, the current will follow a path of least resistance and may travel along a line from the point of one electrical connection to the other. In this situation, the heating might not be as efficient as desired. Therefore, in some configurations, it may be desirable for the humidifier to be configured so that electric current is spread substantially evenly across the heater to improve the efficiency of the heater. For example, as illustrated in FIGS. 6 to 13, the humidifier may comprise a heater comprising an electrically conductive material, such as an ECP structure. In some configurations, as demonstrated in FIGS. 7 and 8, the heater 150 may directly or indirectly interface with an electrical structure 152. In some configurations, as demonstrated in FIG. 6 the electrical structure may comprise a pair of electrically conducting members 151A, 151B extending across opposing sides of the heater 150. For example, the electrically conducting members may be located on opposing surfaces at opposing sides of the heater 150 or the electrically conducting members may be located on the same surface but at opposing sides of the heater 150. In some configurations, the electrically conducting members may be metallic members, such as aluminium bars. In some configurations, multiple electrically conducting members are positioned across opposing sides of the heater 150. For example, two or more electrically conducting members may be arranged in line to lie along a first side of the heater 150 and two or more electrically conducting members may be arranged in a line to lie along a second side of the heater 150, the second side being located opposite the first side. The electrically conducting members may be directly or indirectly electrically connected to a power supply so that, in use, electric current may pass along one electrically conducting member and through the heater 150 to the other electrically conducting member. The electrically conducting members may be electrically connected with the heater 150 and a power supply using any suitable configuration. For example, the electrically conducting members may simply contact the heater or may be adhered, welded, overmoulded or mechanically fastened to the heater 150. In some configurations, the heater 150 is supported by a pair of clamps 152 located on opposite sides of the heater, as shown in FIG. 7. Each clamp may comprise an electrically conducting member, which may be a metal bar, or substantially the entire clamp may form an electrically conducting member. Each electrically conducting member may be positioned to lie along one side of the heater. In use, electric current E may be caused to move through the heater 150 from one electrically conducting member to the other, as shown in FIGS. 6 and 7. By positioning the electrically conducting members to lie along the length or width of the heater, the current may be substantially evenly spread across the heater. In some configurations, at least one electrically conducting member may comprise a printed circuit board (PCB). The PCB may have sensing functions and may comprise a thermistor, thermocouple, or other sensors or sensing modules that may be used to help control operation of the humidifier or other parts of a respiratory therapy system.

Figure 8A:
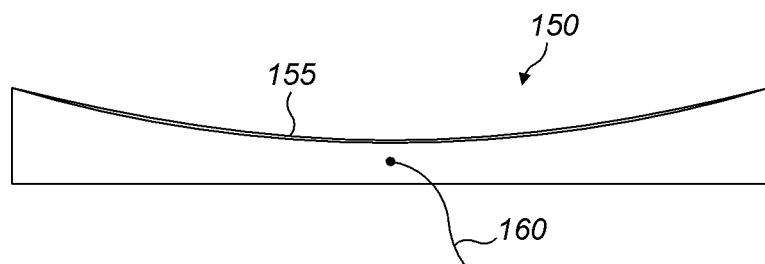
FIG. 8A illustrates a side view of a configuration for a humidifier heater.
Figure 8B:
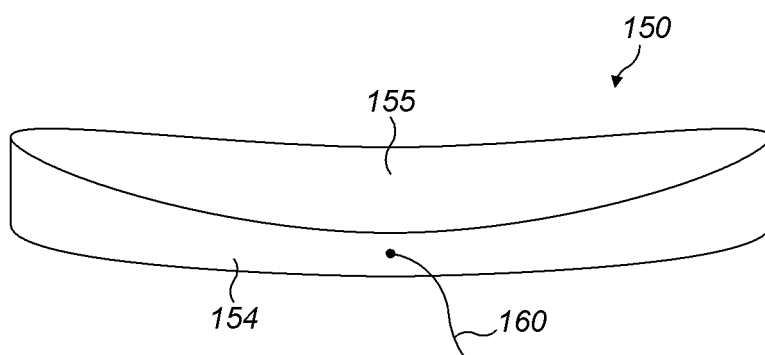
FIG. 8B illustrates a perspective view of the humidifier heater of FIG. 8A.
Figure 9A:
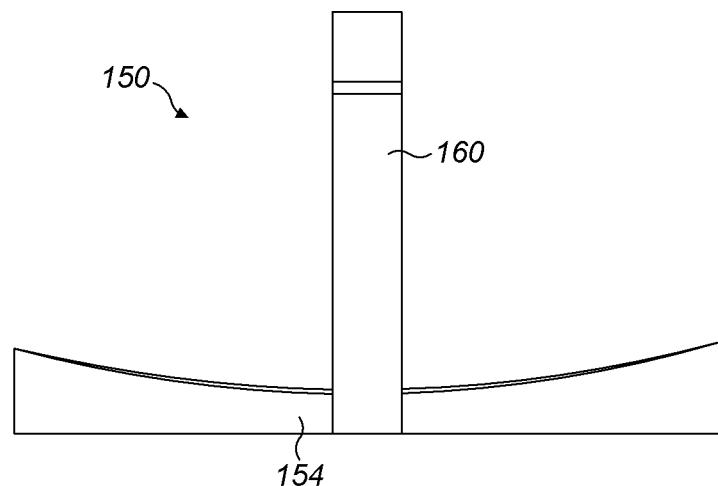
FIG. 9A illustrates a side view of a configuration for a humidifier heater.
Figure 9B:
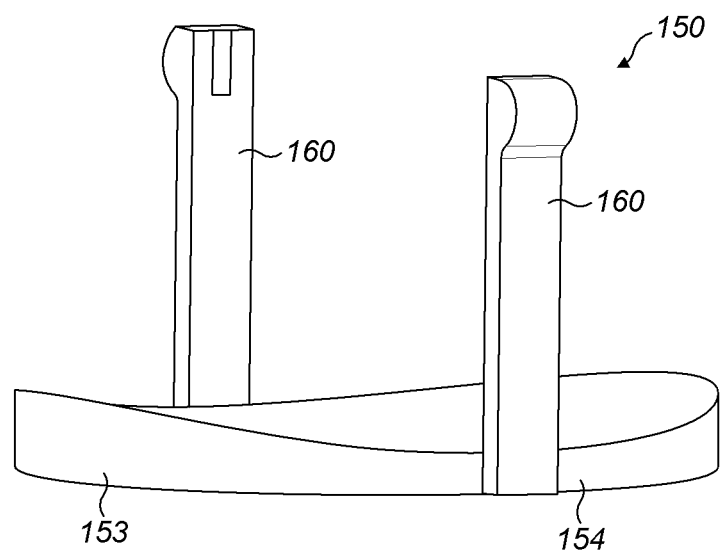
FIG. 9B illustrates a perspective view of the heater of FIG. 9A.
Figure 9C:
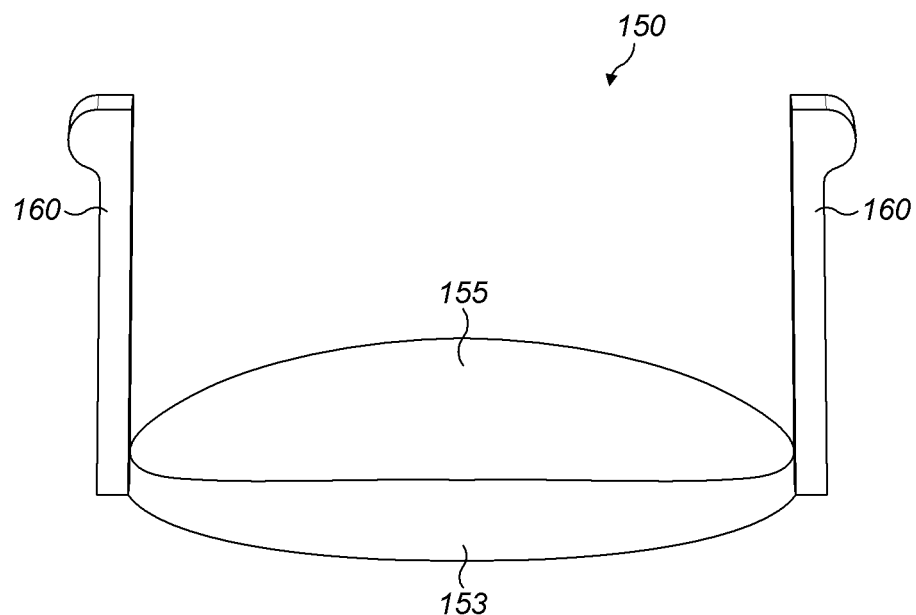
FIG. 9C illustrates another perspective view of the heater of FIG. 9A.
Figure 9D:
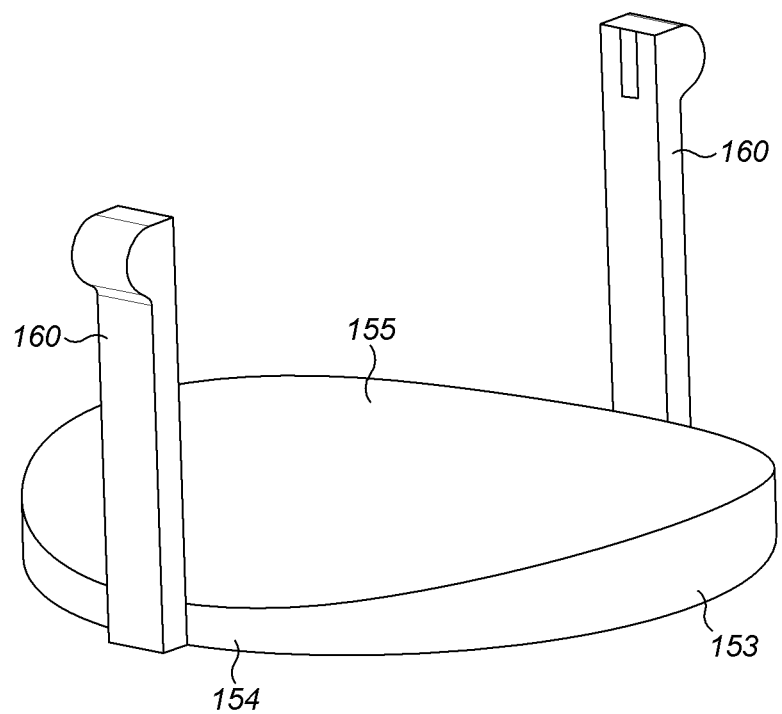
FIG. 9D illustrates yet another perspective view of the heater of FIG. 9A.
Figure 10:
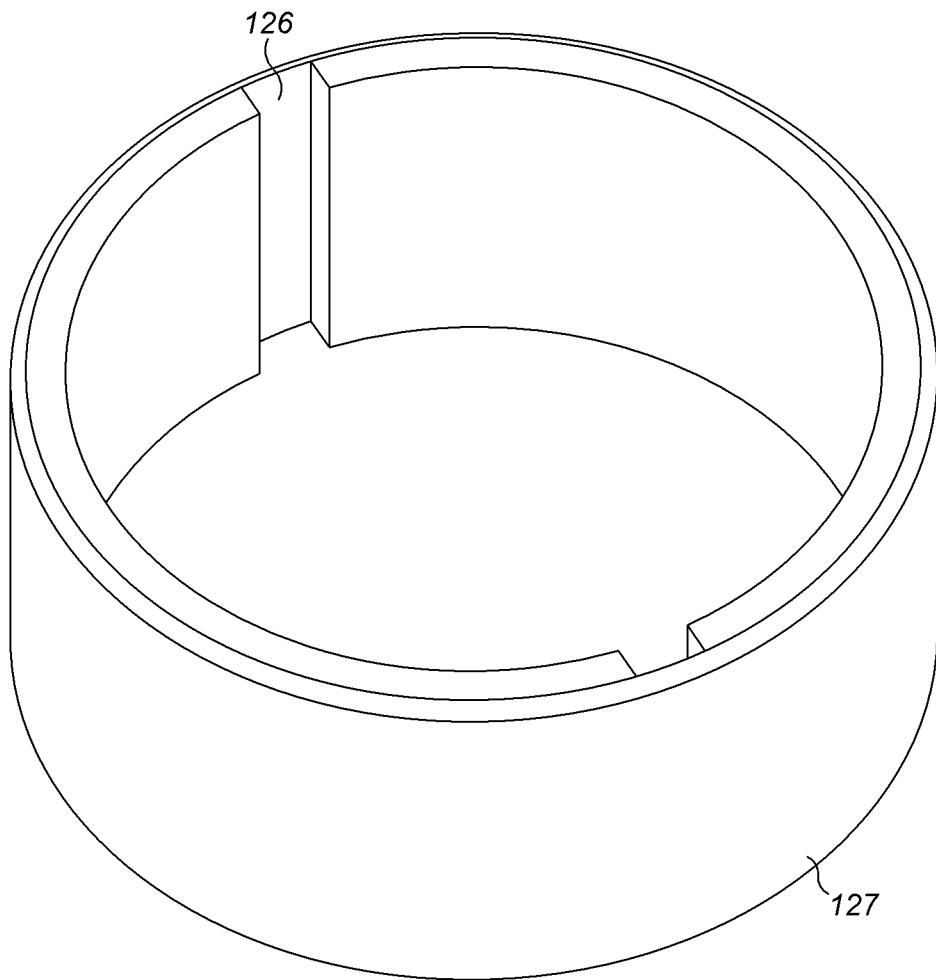
FIG. 10 illustrates a configuration for a humidifier chamber.
Figure 11:
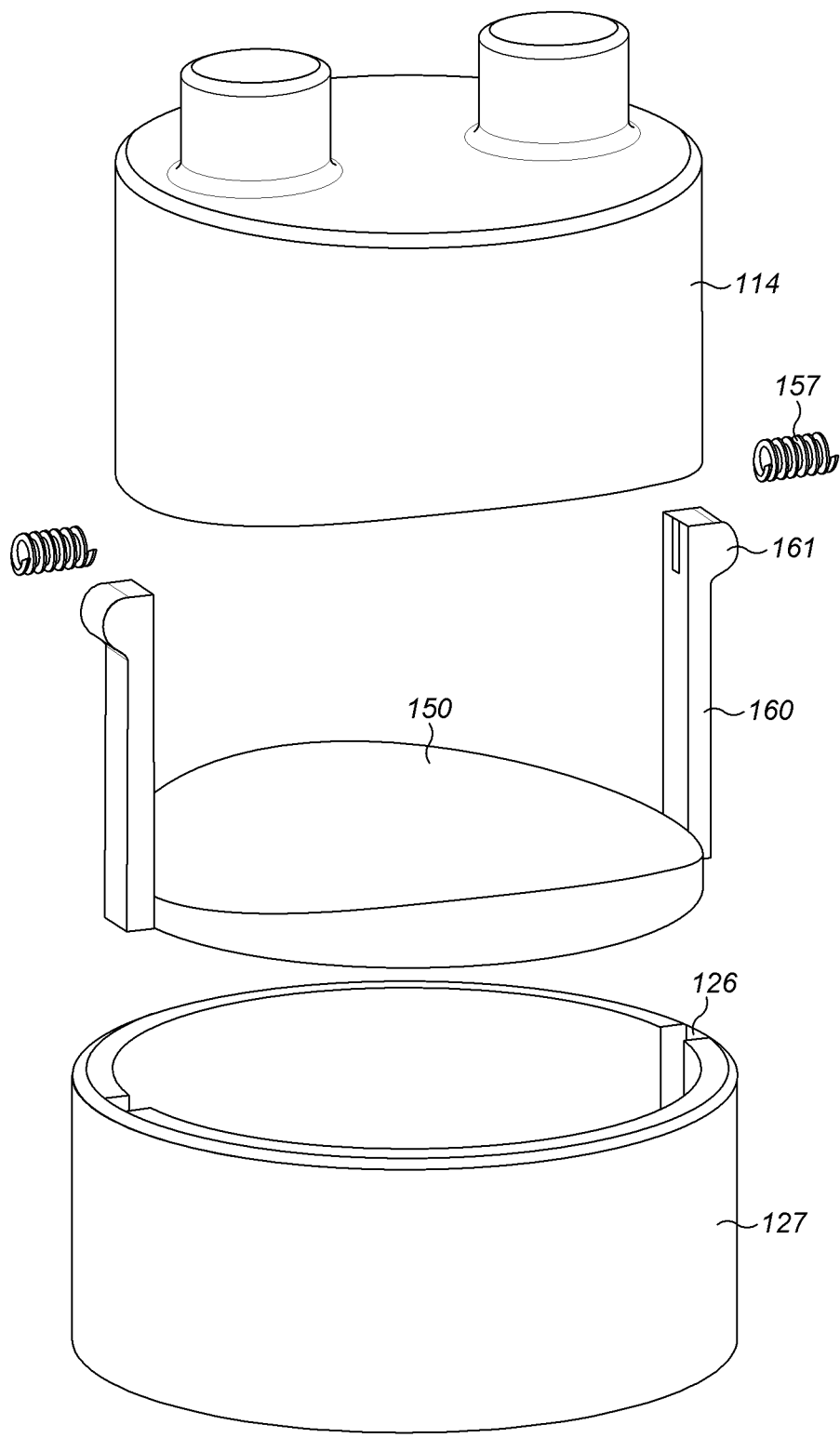
FIG. 11 illustrates an exploded view of a configuration for a humidifier.
Figure 12:
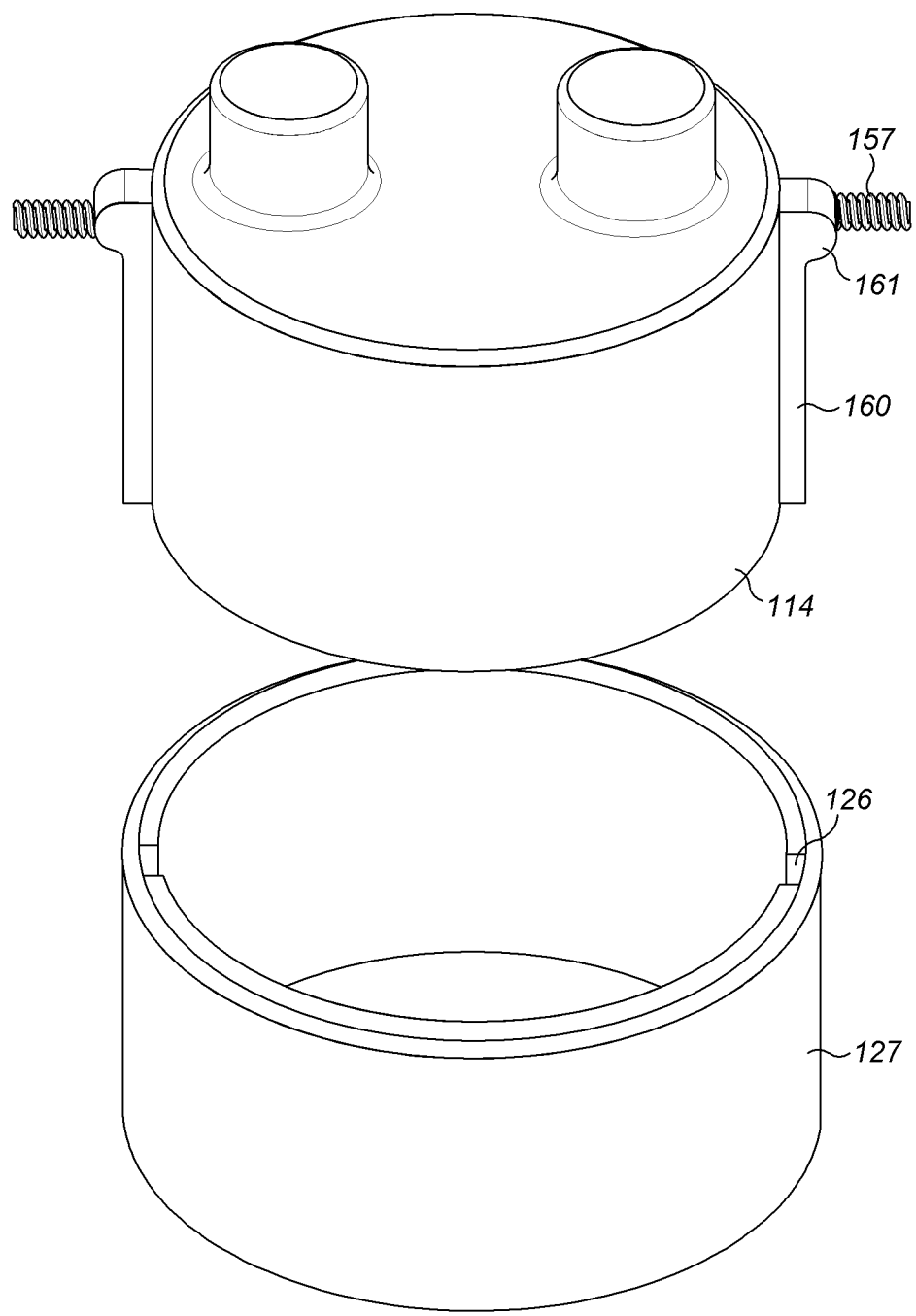
FIG. 12 illustrates a partially exploded view of the configuration of FIG. 11.
Figure 13:
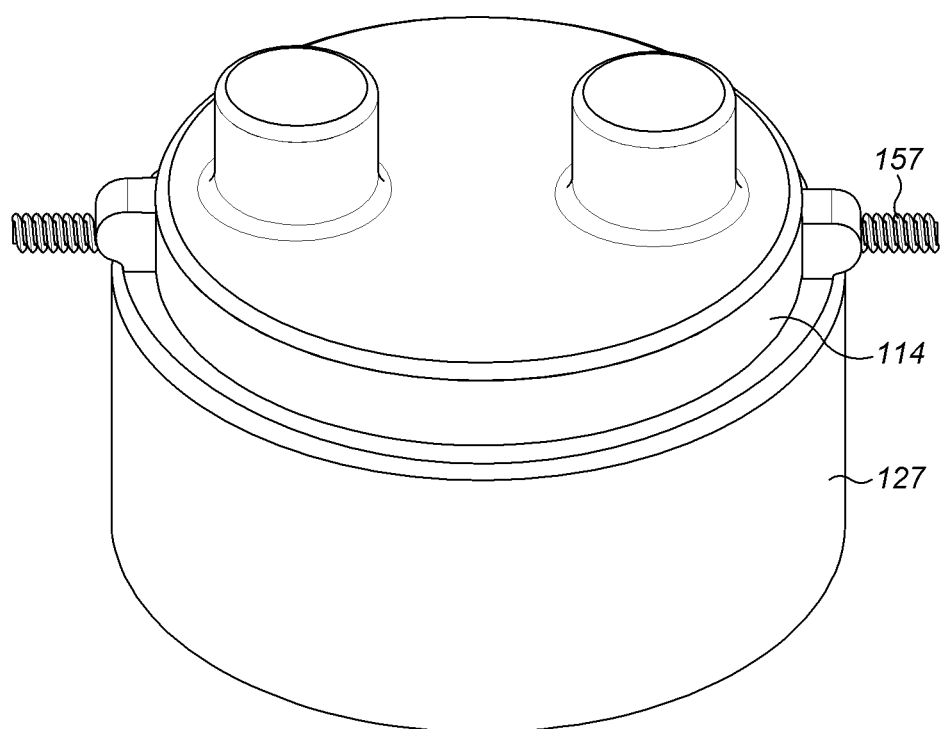
FIG. 13 illustrates a perspective view of a configuration for a humidifier.

The humidifier heater 150 may comprise an electrically conductive material, such as an ECP structure or a metal. In some configurations, as shown in FIGS. 8A to 14, the heater 150 comprises a first edge 153 and a second edge 154. The second edge 154 may be viewed at approximately 90 degrees from the first edge 153 along the same plane. The heater 150 also has a contoured first surface 155 that comprises a pair of crests separated by a trough-like depression extending in one direction along the heater 150. In this configuration, as demonstrated in FIGS. 8A, 8B, and 9A to 9D, the first surface 155 of the heater 150 has a substantially convex profile when viewed from the first edge 153 and has a substantially concave profile when viewed from the second edge 154. The second edge 154 has a minimum thickness at one point or section to form a trough that extends across the heater 150 from the second edge 154 to the opposing edge. The point or section at which the heater 150 is of a minimum thickness may be located at a central region of the second edge 154. Alternatively, the point or section of minimum thickness may be located off centre or near one side of the second edge 154 to encourage differential heating. In effect, the heater 150 may have a variable thickness along its length and/or width. In some configurations, as shown in FIGS. 8A, 8B and 9A to 9D, the heater 150 is substantially circular. However, it is envisaged that the heater 150 may be of any suitable shape, including angled shapes, curved shapes, regular shapes, and irregular shapes. The heater 150 may directly or indirectly interface with an electrical connection configured to provide electrical energy to the heater 150. In some configurations, as illustrated in FIGS. 8A, 8B and 9A to 9D, the heater 150 may comprise a pair of electrical connectors 160 to connect the heater 150 to an electrical connection. One electrical connector 160 may be connected to the heater 150 at opposing ends of the trough, as shown in FIGS. 8A and 8B. In some configurations, the electrical connectors 160 may be connected to electrical connections provided on the humidifier chamber 127 or reservoir 114. For example, the base of the chamber 127 or reservoir 114 may comprise electrical connections, such as electrical wires that are connected to a power supply. Alternatively, the base of the chamber 127 or reservoir 114 may comprise any other form of electrical connection that may be directly or indirectly connected to a power supply. In some configurations, the electrical connectors 160 may comprise one or more electrically conducting arms. The arms 160 may be integrally formed with the heater 150 or the arms 160 may be attached to the heater 150. The arms 160 may be configured to connect the heater 150 to an electrical connection for supplying electrical energy to the heater. For example, each arm 160 may comprise an electrical contact 161 configured to connect with an electrical connection on the chamber 127, reservoir 114 or other part or region of the humidifier. In some configurations, the electrical contact 161 is provided at a distal end of each arm 160. For example, each electrical contact may be located on an extension member that projects from the distal end of each arm 160, as illustrated in FIGS. 9A to 13. In some configurations, as shown in FIG. 11, the electrical contact 161 on each arm 160 may be configured to connect with an electrical connection in the form of a spring 157. Each spring 157 may be configured to connect to the heater 150 and to also directly or indirectly connect to a power supply. The spring contacts 157 may help to maintain the integrity of the electrical connections when the humidifier is moved or is moving. In some configurations, the heater may form the base of the reservoir and/or the base of the humidification chamber for a humidifier. For example, as illustrated in FIGS. 11 to 13, the heater 150 may form the base of the reservoir 114. The reservoir 114 comprises a continuous wall or walls configured to fit between the electrically conducting arms 160 of the heater 150, as shown in FIG. 11. The reservoir 114 may be held between the arms 160 of the heater, as demonstrated in FIG. 12. The reservoir 114 (with heater) may be fitted within the humidifier chamber 127, as shown in FIG. 13. In some configurations, the chamber 127 comprises a continuous wall or walls having an inner surface or surfaces on which recessed channels 126 are provided. The channels 126 are positioned to correspond with the arms 160 of the heater, so that the reservoir 114 and heater 150 can be slid into the chamber 127 by sliding the arms 160 of the heater along the channels 126. The projecting extension member of each arm 160 may extend beyond the outer periphery of the chamber 127, as demonstrated in FIG. 13. In this configuration, the electrical contacts 161 provided on each extension member may directly connect with an electrical connection or the electrical contacts may connect with an electrical connection via spring contacts 157, as described above. In some configurations, each arm may comprise an electrical contact that connects with an electrical connection provided within the respective channel of the chamber. In such configurations, it may not be necessary for each arm to comprise a projecting extension member at or near its distal end. In use, electrical energy may pass through the heater from one electrical connector to another. In some configurations, the electrical energy may pass through the heater along multiple pathways that are spread substantially evenly across the heater, according to Pouillet's law:

$$R = \rho \frac{l}{A}$$

Where:
ρ: electrical resistivity ($\Omega m^{-1}$)
l: length of the heater (m)
A: cross sectional area of the heater ($mm^2$)

Figure 14:
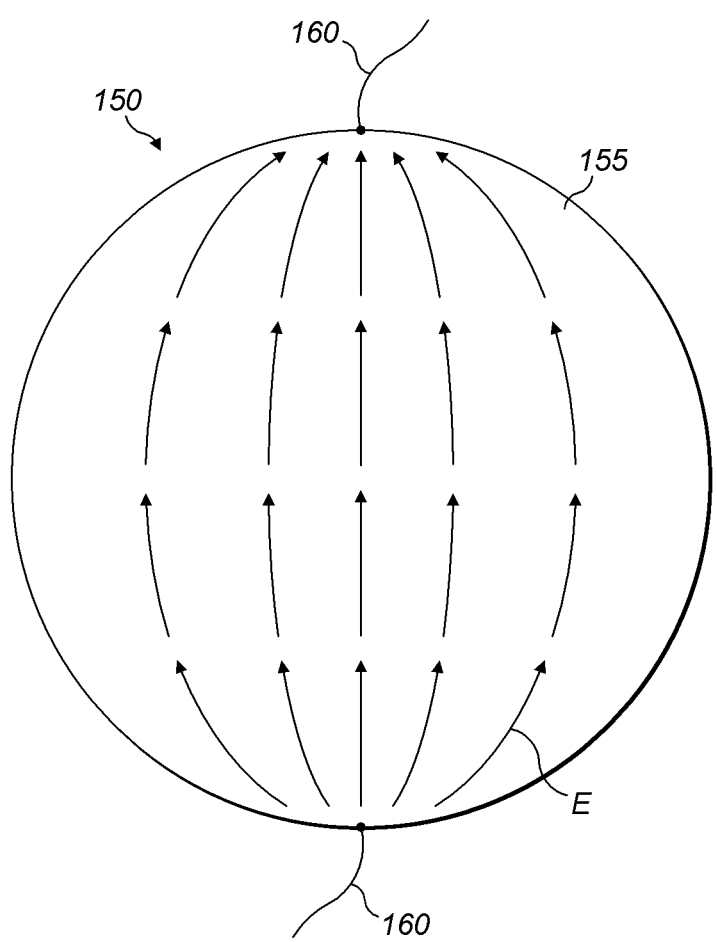
FIG. 14 shows a schematic diagram of current pathways across a configuration for a humidifier heater.

In some configurations, each pathway of electric current E may form an arc between the electrical connections, as shown in FIG. 14. By passing electric current across a significant area of the heater 150, the heater 150 is able to heat a body of water in the reservoir 114 at a faster rate than if current was passed through the heater 150 along a line.

Figure 15A:
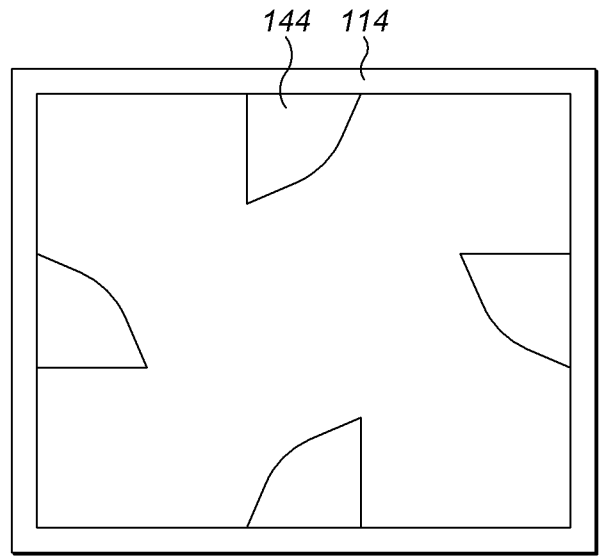
FIG. 15A shows a top view of a reservoir comprising internal vanes.

In some configurations, and as demonstrated in FIG. 15A, the walls of the reservoir 114 may comprise vanes 144.

Figure 15B:
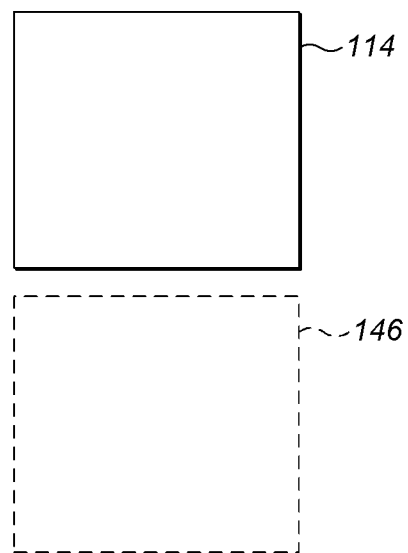
FIG. 15B shows a top view of a reservoir and an insert adapted to be used with the reservoir.
Figure 15C:
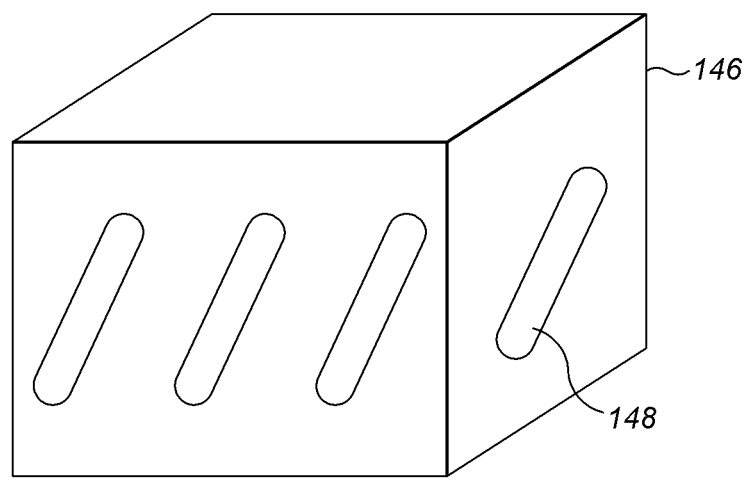
FIG. 15C shows a perspective view of an insert adapted to be used with a reservoir.

When the reservoir 114 contains water and is being heated, the vanes 144 may serve to direct water moving around in the reservoir 114 (e.g., due to convection currents arising from the heating of the reservoir 114). The vanes 144 may then serve to create additional turbulence, vortices, and/or swirling in the reservoir 114, which may improve the efficiency of heating and/or mixing the water. In some configurations, the vanes 144 may be heated. For example, the vanes 144 may be constructed at least in part from an ECP material that may be heated through the use of a power source and electrical connections similarly to those described elsewhere in this disclosure. Heating the vanes 144 can further promote the creation of turbulence, vortices and/or swirling in the reservoir 114 by differentially heating water in the reservoir 114. In some configurations, and as shown in FIGS. 15B and 15C, the reservoir 114 may comprise an insert 146 that may be removably located within the reservoir 114. The insert 146 may comprise features 148. The features 148 may comprise orifices and/or vanes 144, for example but without limitation. The orifices may have an angular shape, a 'teardrop' shape, a curved shape, or some other shape, for example but without limitation. Similarly, the insert 146 may be used to direct water moving around in the reservoir 114 (e.g. due to convection currents arising from the heating of the reservoir 114), which may create additional turbulence, vortices, and/or swirling in the reservoir 114, which may improve the efficiency of heating and/or mixing the water.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Unless the context clearly requires otherwise, throughout the description and claims, the words 'connect', 'connected', 'connecting', 'connects', and the like, when used to refer to electrical connections, should be interpreted to include any suitable form of electrical connection where electrical energy is transferred from one electrically conducting material to another. For example, the electrical connection may be a direct physical connection, such as physical contact between two electrically conducting materials, or the electrical connection may be a wireless connection, such as that provided by inductive charging or resonant inductive coupling or any other suitable system of wirelessly transferring electrical energy between electrically conducting materials.

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

Reference to any prior art in this specification is not, and should not be taken as, an acknowledgement or any form of suggestion that prior art forms part of the common general knowledge in the field of endeavour in any country in the world.

Certain features, aspects and advantages of some configurations of the present disclosure have been described with reference to use by a patient or user. However, certain features, aspects and advantages of the use of the respiratory humidifier as described may be advantageously practiced by other people on behalf of the patient, including medical professionals, medical device dealers, or medical device providers. Certain features, aspects and advantages of the methods and apparatus of the present disclosure may be equally applied to usage by other people.

Additionally, certain features, aspects and advantages of some configurations of the present disclosure have been described with reference to ECP structures and/or materials. However, certain features, aspects and advantages of some configurations of the present disclosure may be advantageously practiced with other materials including metals or ceramics. Certain features, aspects and advantages of the systems and/or apparatus of the present disclosure may equally be applied when using structures and/or materials that are not ECP structures and/or materials.

Additionally, certain features, aspects and advantages of some configurations of the present disclosure have pointed to the use of ECP structures and/or materials with humidifiers, in some cases respiratory humidifiers for use with respiratory therapy systems. However, certain features, aspects and advantages of some configurations of the ECP structures and/or materials may be advantageously utilized with other components of respiratory therapy systems (e.g. for a conduit heater of a respiratory therapy system, etc), with nonmedical humidifiers or with other devices. Certain features, aspects and advantages of the present disclosure may equally be applied when using the ECP structures and/or materials with other systems or devices.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A humidifier comprising:
   a reservoir; and
   an electrically conducting plastic (ECP) structure for heating liquid in the reservoir,
   wherein the ECP structure comprises an ECP layer and a first supporting layer, wherein the ECP layer is in physical communication with the first supporting layer, and
   a second supporting layer.

2. The humidifier of claim 1, wherein the ECP layer is disposed between the first supporting layer and the second supporting layer.

3. The humidifier of claim 1, wherein the first supporting layer comprises a film.

4. The humidifier of claim 1, wherein the ECP structure is located in or forms part of the reservoir.

5. The humidifier of claim 1, wherein the ECP structure is located in or forms part of a chamber for receiving the reservoir.

6. The humidifier of claim 1, wherein the ECP layer comprises a section of an ECP material and a section of another material.

7. The humidifier of claim 6, wherein the ECP layer has an irregular thickness along the width and/or the length of the ECP layer.

8. The humidifier of claim 1, wherein the ECP layer comprises alternating sections of an ECP material and one or more other materials.

9. The humidifier of claim 1, wherein the ECP layer comprises a serpentine track of an ECP material in or on another material.

10. The humidifier of claim 1, wherein the ECP structure is configured to receive electrical or thermal energy.

11. The humidifier of claim 1, wherein the ECP layer comprises intrinsically electrically conductive plastics or polymers.

12. The humidifier of claim 1, wherein the ECP layer comprises an electrically conducting additive or doping agent.

13. The humidifier of claim 1, wherein the ECP layer interfaces with an electrical structure configured to convey electrical and/or thermal energy to the ECP layer.

14. The humidifier of claim 1, wherein the first supporting layer comprises an electrically insulative material.

15. A humidifier comprising:
 a reservoir; and
 an electrically conducting plastic (ECP) structure for heating liquid in the reservoir,
 wherein the ECP structure comprises an ECP layer and a first supporting layer, wherein the ECP layer is in physical communication with the first supporting layer, wherein the first supporting layer comprises a thermally conductive material.

16. The humidifier of claim 15, wherein the ECP structure is located in or forms part of the reservoir.

17. The humidifier of claim 15, wherein the ECP structure is configured to receive electrical or thermal energy.

18. The humidifier of claim 15, wherein the ECP layer interfaces with an electrical structure configured to convey electrical and/or thermal energy to the ECP layer.

19. A humidifier comprising:
 a reservoir; and
 an electrically conducting plastic (ECP) structure for heating liquid in the reservoir,
 wherein the ECP structure comprises an ECP layer and a first supporting layer, wherein the ECP layer is coupled to the first supporting layer, wherein the ECP structure is located in or forms part of a chamber for receiving the reservoir.

20. The humidifier of claim 19, wherein the ECP layer comprises a section of an ECP material and a section of another material.

* * * * *